United States Patent
Aziz et al.

(10) Patent No.: US 10,510,920 B2
(45) Date of Patent: Dec. 17, 2019

(54) SILANIZED ITO ELECTRODE WITH ITO NANOPARTICLES FOR AQUEOUS SULFIDE DETECTION

(71) Applicant: KING FAHD UNIVERSITY OF PETROLEUM AND MINERALS, Dhahran (SA)

(72) Inventors: Md. Abdul Aziz, Dhahran (SA); Zain Hassan Abdallah Yamani, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/886,647

(22) Filed: Feb. 1, 2018

(65) Prior Publication Data
US 2019/0237614 A1     Aug. 1, 2019

(51) Int. Cl.
| | |
|---|---|
| H01L 31/18 | (2006.01) |
| G01N 27/12 | (2006.01) |
| G01N 27/327 | (2006.01) |
| G01N 33/68 | (2006.01) |
| G01N 27/416 | (2006.01) |
| H01L 31/0384 | (2006.01) |
| G01N 27/30 | (2006.01) |
| C23C 14/06 | (2006.01) |
| H01L 31/0224 | (2006.01) |
| G01N 27/42 | (2006.01) |

(52) U.S. Cl.
CPC ...... *H01L 31/1884* (2013.01); *C23C 14/0682* (2013.01); *G01N 27/127* (2013.01); *G01N 27/305* (2013.01); *G01N 27/3277* (2013.01); *G01N 27/4167* (2013.01); *G01N 27/423* (2013.01); *G01N 33/68* (2013.01); *H01L 31/022475* (2013.01); *H01L 31/022483* (2013.01); *H01L 31/03845* (2013.01)

(58) Field of Classification Search
CPC ................................ C12Q 1/004; G02F 1/155
USPC ............................................. 435/14; 359/266
See application file for complete search history.

(56) References Cited

U.S. PATENT DOCUMENTS

| | | | |
|---|---|---|---|
| 9,606,078 B2 | 3/2017 | Patel | |
| 2005/0130248 A1* | 6/2005 | Willner | C12Q 1/004 435/14 |
| 2014/0218781 A1* | 8/2014 | Kobayashi | G02F 1/155 359/266 |

OTHER PUBLICATIONS

Md. Abdul Aziz, et al. "Preparation of Indium Tin Oxide Nanoparticle-modified 3-Aminopropyltrimethoxysilane-functionalized Indium Tin Oxide Electrode for Electrochemical Sulfide Detection", Electroanalysis, Jul. 2017, 8 pages.
R. Pruna., et al., "Organosilane-functionalization of nanostructured indium tin oxide films", Interface Focus, vol. 6, The Royal Society, Oct. 21, 2016, 8 pages.

(Continued)

*Primary Examiner* — Khanh T Nguyen
(74) *Attorney, Agent, or Firm* — Oblon, McClelland, Maier & Neustadt, L.L.P.

(57) ABSTRACT

A silanized ITO electrode modified with ITO nanoparticles is described. ITO nanoparticles of cubic and semispherical shapes are immobilized on a silanized ITO film. The electrode may be used in an electrolytic cell to detect aqueous sulfide with a 0.5-1.4 µM limit of detection. The electrode shows high specificity towards aqueous sulfide and a high reproducibility in measurement.

20 Claims, 7 Drawing Sheets

(56) References Cited

OTHER PUBLICATIONS

R. Pruna., et al., "Towards Nanostructured ITO-Based Electrochemical Sensors: Fabrication, Characterization and Functionalization", Proceedings of Eurosensors 2017, Sep. 3-6, 2017, 1, 4 pages.
Ming-Yuan Wei, et al., "High catalytic activity of indium tin oxide nanoparticle modified electrode towards electro-oxidation of ascorbic acid", Journal of Electroanalytical Chemistry, Nov. 4, 2011, 5 pages.

* cited by examiner

FIG. 5A  FIG. 5B

SILANIZED ITO ELECTRODE WITH ITO NANOPARTICLES FOR AQUEOUS SULFIDE DETECTION

STATEMENT OF ACKNOWLEDGEMENT

This project was prepared with financial support from King Abdulaziz City for Science and Technology (KACST) through the Science & Technology Unit at King Fand University of Petroleum & Minerals (KFUPM): Project no. 14-ENV332-04, as part of the National Science, Technology and Innovation Plan.

STATEMENT REGARDING PRIOR DISCLOSURE BY THE INVENTORS

Aspects of this technology are described in the article: M. A. Aziz, W. Mahfoz, M. Nasiruzzaman Shaikh, M. H. Zahir, A.-R. Al-Betar, M. Oyama, D. Theleritis, and Z. H. Yamani, "Preparation of Indium Tin Oxide Nanoparticle-modified 3-Aminopropyltrimethoxysilane-functionalized Indium Tin Oxide Electrode for Electrochemical Sulfide Detection" published in *Electroanalysis*, 2017, 29, 1683-1690, on 4 Apr. 2017, and is incorporated herein by reference in its entirety.

BACKGROUND OF THE INVENTION

Technical Field

The present invention relates to a silanized ITO electrode modified with ITO nanoparticles, a method of making the electrode, and a method of using the electrode for detecting aqueous sulfide.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Sulfide anion is one of the most harmful species to the environment and general public health as a consequence of the toxicity of $H_2S$ [Government of Alberta Employment and Immigration, *Work place health and safety bulletin: Hydrogen Sulphide at the Work Site*, 2010 WHS-PUB-CH029.pdf; M. K. Amosa, et al. *NAFTA*, 2010, 61, 85-92; US Department of Health and Human Services, Agency for Toxic Substances and Disease Registry, *Toxicological Profile for Hydrogen Sulfide and Carbonyl Sulfide*, 2014 tp114.pdf; Y. Chen, et al. *Electrochimica Acta*, 2016, 205, 124-131—each incorporated herein by reference in its entirety]. In aqueous solutions, sulfide exists mainly as $S^{2-}$ and $HS^-$ species, as well as $H_2S$ (depending on the ambient pH) [M. K. Amosa, et al. *NAFTA*, 2010, 61, 85-92—incorporated herein by reference in its entirety]. Sulfides are generated in various industrial settings and activities such as drilling and refinement of petroleum and natural gas, combustion of logistic fuels (kerosene, coal, gasoline, diesel, etc.), waste treatment plants, tanneries, and paper mills [M. K. Amosa, et al. *NAFTA*, 2010, 61, 85-92; US Department of Health and Human Services, Agency for Toxic Substances and Disease Registry, *Toxicological Profile for Hydrogen Sulfide and Carbonyl Sulfide*, 2014 tp114.pdf; S. K. Pandey, et al. *Trends in Analytical Chemistry*, 2012, 32, 87-99; D. Riddle, *Danger and detection of hydrogen sulphide gas in oil and gas exploration and production*, Det-Tronics, United Technologies Corp. 2009; N. S. Lawrence, et al. *Talanta*, 2000, 52, 771-784; C. Bohnke, et al. *Solid State Ionics*, 2014, 262, 279-282—each incorporated herein by reference in its entirety]. The potent threats to humans that exposure to sulfide anions pose include several diseases that these anions lead to, such as neurological and cardiovascular disorders, conjunctivitis, photophobia, corneal bullae, tearing, pain and blurred vision [M. K. Amosa, et al. *NAFTA*, 2010, 61, 85-92; US Department of Health and Human Services, Agency for Toxic Substances and Disease Registry, *Toxicological Profile for Hydrogen Sulfide and Carbonyl Sulfide*, 2014 tp114.pdf; Y. Chen, et al. *Electrochimica Acta*, 2016, 205, 124-131; S. K. Pandey, et al. *Trends in Analytical Chemistry*, 2012, 32, 87-99; D. Riddle, *Danger and detection of hydrogen sulphide gas in oil and gas exploration and production*, Det-Tronics, United Technologies Corp. 2009; N. S. Lawrence, et al. *Talanta*, 2000, 52, 771-784; C. Bohnke, et al. *Solid State Ionics*, 2014, 262, 279-282; Matheson Tri-Gas, Inc., *Lower and Upper Explosive Limits for Flammable Gases and Vapors (LEL/UEL)*, 2007; X. Hu, et al. *Reviews in Analytical Chemistry*, 2013, 32, 247-256—each incorporated herein by reference in its entirety]. Also, exposure to even low amounts of sulfide causes physiological distress [C. Bohnke, et al. *Solid State Ionics*, 2014, 262, 279-282—incorporated herein by reference in its entirety]. In addition to the health issues that arise from the release of $H_2S$, sulfides aggressively corrode many metals such as steel and copper. Corrosion is a major concern in many industrial installations such as sulfide ore mills, deep oil and gas wells, pipelines transporting sour oil, and paper factories [Y. E. Mendili, et al. *RSC Advances*, 2013, 3, 15148-15156—incorporated herein by reference in its entirety]. Since the sulfide ion is water soluble, the ability to selectively and sensitively detect it in the aqueous phase is very relevant.

Analytical methods for monitoring sulfides include colorimetric, titrimetric, spectroscopic, and gas chromatography based methods as well as electrophoretic and electrochemical techniques, as summarized in several reviews [N. S. Lawrence, et al. *Talanta*, 2000, 52, 771-784; T. Xu, et al. *Analyst*, 2016, 141, 1185-1195; M. Zlamalova, et al. *Monatsh Chem*, 2016, 147, 1331—each incorporated herein by reference in its entirety]. However, most of these classical methods require complicated instrumentation and are time-consuming. The electrochemical techniques, however, do offer economical, accessible, sensitive, and rapid ways to detect sulfides. Among the developed electrochemical methods, those based on the direct electrocatalytic oxidation of sulfides on bare or modified electrodes have attracted considerable attention due to their simplicity and ability to detect sulfide in a straightforward manner. A variety of bare working electrodes including platinum, gold, graphite and glassy carbon have been used to electro-oxidize sulfides [T. Loučka, *Journal of Electroanalytical Chemistry and Interfacial Electrochemistry*, 1971, 31, 319-332; A. M. El-Shamy, et al. *Chemical Sciences Journal*, Volume 2010: CSJ-10, 1-12; X. Gao, et al. *Langmuir*, 1992, 8, 668-672; J. Lawrence, et al. *Analytical Sciences*, 2007, 23, 673-676—each incorporated herein by reference in its entirety]. The electrochemical behavior of sulfides on these bare electrodes, however, has shown numerous problems. For example, the high affinity of sulfide or oxidized forms of sulfide for the electrode surface and the resulting poisoning of the electrode surface by these species have been shown to yield poor analytical signals [A. M. El-Shamy, et al. *Chemi-* cal Sciences Journal, Volume 2010: CSJ-10, 1-12; A. Chira, et al. U.P.B. Sci. Bull., Series B, 2012, 74, 183-192; Y. Sung, et al. Electrochimica Acta, 1998, 44, 1019-1030; B. Thakur, et al. Journal of Carbon Research, 2016, 2, doi:10.3390/c2020014—each incorporated herein by reference in its entirety]. Due to this poisoning problem, Thakur et al. showed the possibility of using screen-printed graphite electrodes as disposable electrodes, i.e., electrodes that are intended to be discarded after being used for one measurement. Their detection limit for sulfides, however, was found to be quite high, at 32.5 µM [B. Thakur, et al. Journal of Carbon Research, 2016, 2, doi:10.3390/c2020014—incorporated herein by reference in its entirety]. On the other hand, some bare electrodes require a high overpotential to electro-oxidize sulfides [A. M. El-Shamy, et al. Chemical Sciences Journal, Volume 2010: CSJ-10, 1-12; M. Ardelean, et al. Anal. Methods, 2014, 6, 4775-4782; A. Baciu, et al. Sensors, 2015, 15, 14526-14538—each incorporated herein by reference in its entirety], which is a barrier for achieving a selective and sensitive detection. In earlier studies, an electrochemical sulfide sensor was fabricated based on the moderate electrocatalytic properties of bulk indium tin oxide nanoparticles (ITO) electrodes toward sulfide ions [M. A. Aziz, et al. Electroanalysis, 2015, 27, 1268-1275—incorporated herein by reference in its entirety]. This ITO electrode could be used as a highly stable and selective electrode for sensing sulfides. The high stability of the ITO electrode for sensing sulfides is due to its low affinity for sulfide molecules and oxidized forms of sulfide. The high selectivity of the ITO electrode for sulfides is due to its poor electrocatalytic properties towards most interference molecules and electroactive molecules. The detection limit of the bulk ITO electrode for sulfide was measured to be 8 µM [M. A. Aziz, et al. Electroanalysis, 2015, 27, 1268-1275—incorporated herein by reference in its entirety], but many practical applications require lower values. Improving the electrocatalytic properties of ITO with a stable electrocatalyst would appear to be an effective way to sense very low concentrations of the sulfide ion with high selectivity while keeping the electrode stable.

To improve the electrocatalytic properties of the ITO electrode for various electrochemical applications, many strategies have been considered. For example, immobilization of Au, Ag, Pt, Pd, and carbon nanotubes on ITO electrodes have been reported [M. A. Aziz, et al. "Nanomaterials in Electrochemical Biosensor" in Materials for Biomedical Applications, Trans Tech Publication Inc., 2014, pp. 125; M. A. Aziz, et al. Bulletin of the Korean Chemical Society, 2007, 28, 1171-1174; M. A. Aziz, et al. Electroanalysis, 2016, 28, 1119-1125; M. A. Aziz, et al. Chemical Communications, 2008, 4607-4609; P. Bertoncello, et al. Chem. Commun., 2007, 1597-1599; G. Chang, et al. J. Phys. Chem. B, 2005, 109, 1204-1209; X. Chen, et al. Journal of Electroanalytical Chemistry, 2016, 779, 156-160—each incorporated herein by reference in its entirety]. However, these modified electrodes may not have the stability for fabricating a sulfide sensor due to poisoning of electrode surface from sulfide, as discussed in an earlier paragraph for their corresponding bulk electrodes. Recently, in an investigation by Wei et al., an ITO-NP-modified ITO electrode displayed better electrocatalytic properties toward ascorbic acid and dopamine than did the ITO bulk electrode [M. Wei, et al. Journal of Electroanalytical Chemistry, 2012, 664, 156-160—incorporated herein by reference in its entirety]. Wei et al. prepared the ITONP-modified ITO electrode by spin coating a mixture of ITO-NPs and Tween-20 and successive annealing at 450° C. Ideally, this high temperature annealing should be eliminated for process simplification and reduction of the sensor cost [M. Wei, et al. Journal of Electroanalytical Chemistry, 2012, 664, 156-160—incorporated herein by reference in its entirety]. Although some nanomaterial-modified electrodes have been reported for the detection of sulfides, the fabrication of sulfide sensors using ITO-NP modified ITO has not been reported [Y. Chen, et al. Electrochimica Acta, 2016, 205, 124-131; J. Lawrence, et al. Analytical Sciences, 2007, 23, 673-676; S. Devaramani, et al. Int. J. Electrochem. Sci., 2014, 9, 4692-4708; B. Yang, et al. Electrochemistry Communications, 2009, 11, 1230-1233; K. Lin, et al. Int. J. Electrochem. Sci., 2012, 7, 11426-11443; P. Qi, et al. Electroanalysis, 2011, 23, 2796-2801; N. S. Lawrence, et al. Analytica Chimica Acta, 2004, 517, 131-137—each incorporated herein by reference in its entirety].

In view of the forgoing, one objective of the present invention is to provide an ITONP-modified ITO electrode, a method of making the ITONP-modified ITO electrode, and a method of using the ITONP-modified ITO electrode for the detection of aqueous sulfide.

BRIEF SUMMARY OF THE INVENTION

According to a first aspect, the present disclosure relates to an ITONP-modified ITO electrode, comprising a silanized ITO (indium tin oxide) electrode and ITO nanoparticles (ITONP) on the surface of the silanized ITO electrode, wherein the ITO nanoparticles have diameters of 10-210 nm.

In one embodiment, the ITO nanoparticles are in the form of semispherical nanoparticles having diameters of 10-20 nm and/or cubic nanoparticles having widths of 40-120 nm.

In one embodiment, the silanized ITO electrode is made from an ITO electrode having a sheet resistance of 15-45 Ω/sq.

In one embodiment, the ITO nanoparticles are distributed homogenously on the surface of the silanized ITO electrode.

According to a second aspect, the present disclosure relates to a method for producing the ITONP-modified ITO electrode of the first aspect. This method involves reacting an ITO electrode with a solution comprising an alkoxysilane and an alcohol to produce the silanized ITO electrode, then contacting the silanized ITO electrode with an aqueous solution of ITO nanoparticles, and then drying to produce the ITONP-modified ITO electrode.

In one embodiment, the solution comprises 0.5-4 vol % of the alkoxysilane relative to a total volume of the solution.

In one embodiment, the alkoxysilane is 3-aminopropyl trimethoxysilane (APTMS).

In one embodiment, the method does not comprise an annealing step.

In one embodiment, 150-650 µg of ITO nanoparticles are in the aqueous solution for every 1 $cm^2$ of silanized ITO electrode contacted.

In one embodiment, the silanized ITO electrode is contacted by dropping the aqueous solution onto the silanized ITO electrode.

According to a third aspect, the present disclosure relates to an electrolytic cell. The electrolytic cell has a working electrode comprising the ITONP-modified ITO electrode of the first aspect in contact with an electrolyte solution. The electrolytic cell also has a counter electrode comprising platinum in contact with the electrolyte solution. The electrolyte solution comprises 0.1 µM-10 mM aqueous sulfide.

In one embodiment, the electrolytic cell has an aqueous sulfide limit of detection of 1-5 µM for an amperometric measurement of the electrolyte solution.

In one embodiment, the electrolytic cell has an aqueous sulfide limit of detection of 0.5-1.4 μM for a chronocoulometric measurement of the electrolyte solution.

In one embodiment, a chronocoulometric measurement of the electrolytic cell is substantially similar to a second chronocoulometric measurement by an otherwise identical second electrolytic cell further comprising at least one interferent in a second electrolyte solution. The interferent is at least one selected from the group consisting of sulfite, sulfate, chloride, carbonate, acetate, citrate, oxalate, elemental sulfur, benzene, toluene, and xylene.

In one embodiment, the electrolytic cell further comprises a Ag/AgCl reference electrode in contact with the electrolyte solution.

In one embodiment, the electrolyte solution further comprises an inorganic salt at a concentration of 10 mM-1 M.

In one embodiment, the aqueous sulfide originates from hydrogen sulfide gas.

In a further embodiment, the hydrogen sulfide gas is produced by at least one selected from the group consisting of petroleum extraction, petroleum refinement, natural gas extraction, natural gas refinement, fuel combustion, waste water treatment, tanneries, paper mills, and textile manufacturing.

In one embodiment, the electrolytic cell has a reproducible chronocoulometric measurement for five or more electrolyte solutions having substantially similar aqueous sulfide concentrations.

In a further embodiment, the five or more electrolyte solutions have an aqueous sulfide concentration of 10-500 μM.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 5A is an amperogram of an ITONP-modified ITO electrode (produced by drop-drying), in 25 mM Tris buffer and 50 mM $KNO_3$ at pH 8 and +0.3 V, with successive additions of 10 μM, 50 μM, and 100 μM $Na_2S$.

FIG. 5B is a zoomed-in view of FIG. 5A.

DETAILED DESCRIPTION OF THE EMBODIMENTS

Figure 1A:
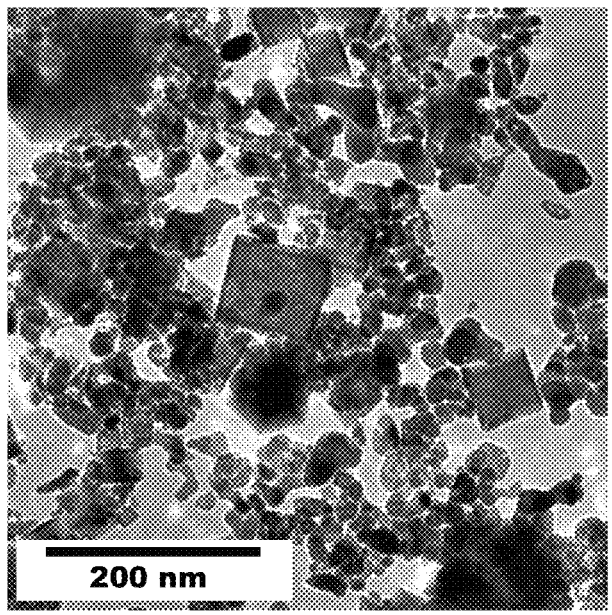
FIG. 1A is a transmission electron microscopy (TEM) image of the ITONP, showing cubic nanoparticles.
Figure 1B:
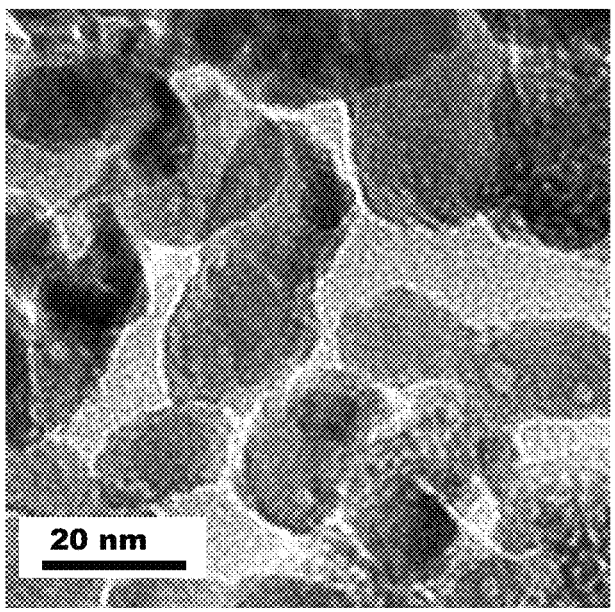
FIG. 1B is another TEM image of the ITONP, showing semispherical nanoparticles.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more."

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

For polygonal shapes, the term "diameter," as used herein, and unless otherwise specified, refers to the greatest possible distance measured from a vertex of a polygon through the center of the face to the vertex on the opposite side. For a circle, an oval, and an ellipse, "diameter" refers to the greatest possible distance measured from one point on the shape through the center of the shape to a point directly across from it. For a cubic particle, the term "width" refers to the length of an edge, while the term "diameter" refers to the length of the diagonal through the cube. For instance, a perfectly-shaped cube with a width of a would have a diameter (diagonal) of $(\sqrt{3})\cdot a$.

As used herein, "compound" is intended to refer to a chemical entity, whether as a solid, liquid, or gas, and whether in a crude mixture or isolated and purified.

As used herein, ITONP refers to a nanoparticle (NP) comprising indium tin oxide (ITO). Additionally, the ITONP-modified ITO electrode may be referred to as "ITONP electrode."

In addition, the present disclosure is intended to include all isotopes of atoms occurring in the present compounds and complexes. Isotopes include those atoms having the same atomic number but different mass numbers. By way of general example and without limitation, isotopes of hydrogen include deuterium and tritium. Isotopes of carbon include $^{13}C$ and $^{14}C$; isotopes of oxygen include $^{16}O$, $^{17}O$, $^{18}O$, and others; isotopes of indium include, but are not limited to, $^{113}In$ and $^{115}In$; isotopes of tin include, but are not limited to, $^{120}Sn$, $^{118}Sn$, and $^{116}Sn$; isotopes of sulfur include, but are not limited to, $^{32}S$, $^{34}S$, $^{33}S$, and $^{36}S$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed.

According to a first aspect, the present disclosure relates to an ITONP-modified ITO electrode, comprising a silanized ITO (indium tin oxide) electrode and ITO nanoparticles (ITONP) on the surface of the silanized ITO electrode, wherein the ITO nanoparticles have diameters of 10-210 nm, preferably 12-150 nm, more preferably 15-120 nm, even more preferably 16-100 nm. However, in some embodiments, the ITO nanoparticles may have diameters smaller than 10 nm or greater than 210 nm.

Indium tin oxide (ITO) is a ternary composition of indium, tin, and oxygen. Depending on the oxygen content, it can either be described as a ceramic or alloy. Indium tin oxide, such as that of the present disclosure, is usually encountered as an oxygen-saturated composition with a formulation of 74 wt % In, 18 wt % $O_2$, and 8 wt % Sn, each relative to a total weight of the composition. In terms of $SnO_2$ and $In_2O_3$, this composition is equivalent to and may be represented as 10 wt % $SnO_2$ and 90 wt % $In_2O_3$, both relative to a total weight of the composition. ITO is transparent and colorless in thin layers, while in bulk form it is yellowish to grey. In the infrared region of the spectrum it acts as a metal-like mirror. Oxygen unsaturated compositions are less common and are termed oxygen-deficient ITO. In other embodiments, the ITO of the present disclosure may comprise oxygen-deficient ITO, or ITO having compositions of In, O, and/or Sn that are different than those in the oxygen-saturated composition. Preferably the ITO of the present disclosure is substantially pure, meaning that the ITO comprises greater than 99.0 wt %, preferably greater than 99.5 wt %, preferably greater than 99.8 wt % the combined weight of indium, tin, and oxide, relative to a total weight of the ITO. Similarly, preferably the ITONP and the ITO film of the ITO electrode comprise greater than 99.0 wt %, preferably greater than 99.5 wt % ITO, each relative to their total weight.

Indium tin oxide is one of the most widely used transparent conducting oxides because of its two main properties: its electrical conductivity and optical transparency, as well as the ease with which it can be deposited as a thin film. As with all transparent conducting films, a compromise must be made between conductivity and transparency, since increasing the thickness and increasing the concentration of charge carriers increases the material's conductivity, but decreases its transparency.

Thin films of indium tin oxide are most commonly deposited on surfaces by physical vapor deposition. Often used is electron beam evaporation, or a range of sputter deposition techniques. The ITO of the present disclosure may be present as a film having a thickness of 15-500 nm, preferably 30-300 nm, more preferably 40-200 nm. To provide stability, preferably the ITO film is attached to a substrate, such as a glass or quartz slide. The ITO electrode, as used herein, comprises the ITO film on a substrate. The glass slide may comprise boro-aluminosilicate glass, sodium borosilicate glass, fused-silica glass, or some other type of glass. Other materials may be used for a substrate, such as polyethylene terephthalate (PET) or a metal. Preferably, however, the substrate does not conduct electricity. The substrate may have a length of 0.5-90 cm, preferably 0.7-10 cm, more preferably 0.8-2 cm, a width of 0.2-90 cm, preferably 0.3-5 cm, more preferably 0.4-1.5 cm, and a thickness of 0.2-2 mm, preferably 0.5-1.5 mm. In another embodiment, the substrate may be circular with a diameter of 0.4-5 cm, preferably 0.5-2 cm and a thickness as mentioned previously. However, in other embodiments, ITO may be deposited on a substrate having a roughened or patterned surface, in order to produce an ITO film having a texturized, rather than a smooth surface. In some embodiments, ITO may be deposited on both sides of a flat substrate.

Preferably the ITO of the ITO film and/or the ITONP is crystalline or nanocrystalline. Where the ITO is nanocrystalline, it may have a grain size of 10-100 nm, preferably 20-80 nm, more preferably 25-70 nm. However, in an alternative embodiment, the ITO may be amorphous.

In alternative embodiments, the ITO of the ITO film and/or ITONP may be mixed or replaced by other conductive compounds, such as aluminum-doped zinc oxide (AZO), gallium-doped zinc oxide (GZO), indium-doped zinc oxide (IZO), carbon nanotubes, graphene, inherently conductive polymers (ICP), silver nanoparticles, gold nanoparticles, or other metals.

In one embodiment, the surface resistivity of the ITO film may be 15-45 Ω/sq, preferably 17-40 Ω/sq, more preferably 25-35 Ω/sq, or about 30 Ω/sq. However, in some embodiments, the surface resistivity may be less than 15 Ω/sq or greater than 45 Ω/sq.

In one embodiment, the ITO electrode may have an area in direct contact with an electrically-conductive material so that the electrode may be attached to a power source or form part of an electrolytic cell. An "electrically-conductive material" as defined here is a substance with an electrical resistivity of at most $10^{-6}$ Ω·m, preferably at most $10^{-7}$ Ω·m, more preferably at most $10^{-8}$ Ω·m at a temperature of 20-25° C. The electrically-conductive material may be platinum-iridium alloy, iridium, titanium, titanium alloy, stainless steel, gold, cobalt alloy, copper, aluminum, tin, iron, and/or some other metal. In other embodiments, a part of the ITO film may extend from the substrate in order to be connected to an electrically-conductive material. An electrically-conductive material may be held in place by solder, a clip, a conductive adhesive, or some other means. Preferably, the ITO electrode is configured to be in contact with a solution in an electrolytic cell.

The silanized ITO electrode being "silanized" means that the ITO film was reacted with an alkoxysilane to form a monolayer of silicone chemically bound to the ITO film. Silicones, also known as polysiloxanes, are polymers that include any inert, synthetic compound made up of repeating units of siloxane, which is a chain of alternating silicon atoms and oxygen atoms, frequently combined with carbon and/or hydrogen. In one embodiment, the ITO film may be silanized with an aminosilane so that the ITO film is functionalized with amine groups. In another embodiment, the ITO film of the ITO electrode may not be saturated with monolayer of silicone, but instead comprise a silicone coverage that is 80-99%, preferably 85-95% of the area of exposed ITO film.

Figure 2A:
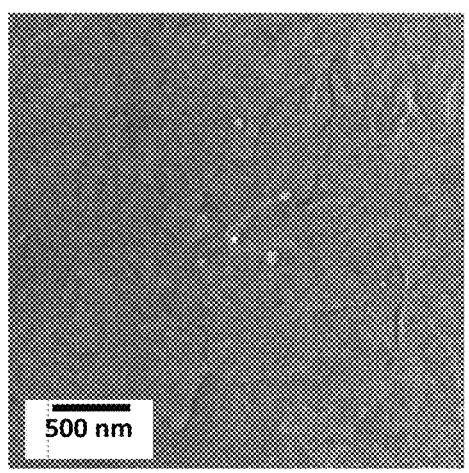
FIG. 2A is a field emission scanning electron microscopy (FESEM) image of a bare (un-silanized) ITO electrode.
Figure 2B:
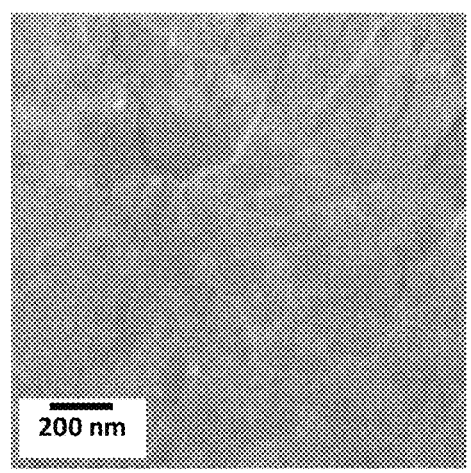
FIG. 2B is another FESEM image of a bare ITO electrode.
Figure 2C:
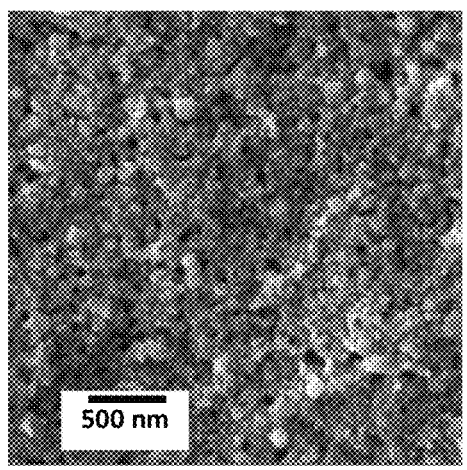
FIG. 2C is a FESEM image of the ITONP electrode produced by drop-drying.
Figure 2D:
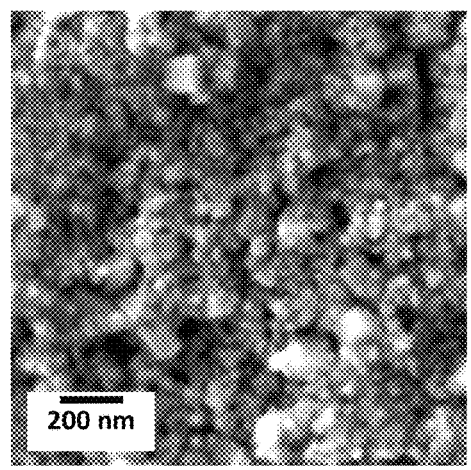
FIG. 2D is another FESEM image of the ITONP electrode produced by drop-drying.

In one embodiment, the ITO nanoparticles are distributed homogenously on the surface of the silanized ITO electrode. This means that the average diameter of regions on the silanized ITO electrode that are free of nanoparticles is no greater than 80 nm, preferably no greater than 60 nm, even more preferably no greater than 40 nm. In one embodiment, at least 95%, preferably at least 97%, more preferably at least 98% of the surface of the silanized ITO electrode is covered with ITO nanoparticles. In a preferred embodiment, the ITO nanoparticles may be distributed homogenously so that the entire silanized ITO electrode, or the entire silanized ITO film, is covered with nanoparticles, forming one or more layers. FIGS. 2C and 2D show FESEM images of ITO nanoparticles being homogeneously distributed on a silanized ITO electrode, and such a homogenous distribution may also be observed by the naked eye.

In one embodiment, an otherwise non-homogeneous distribution of ITO nanoparticles may be made into a homogeneous distribution by depositing a greater number of ITO nanoparticles onto the silanized ITO electrode, and/or by depositing aggregated ITO nanoparticles that have a smaller cluster size. In one embodiment, aggregated or monodisperse ITO nanoparticles may be immobilized on the silanized ITO electrode surface by electrostatic binding.

Preferably, the ITO nanoparticles are monodisperse, or not aggregated. In an alternative embodiment, the ITO nanoparticles are aggregated. The ITO nanoparticles being "aggregated" refers to a clustered particulate composition comprising the ITO nanoparticles being clumped together in such a way so as to form clusters thereof, at least 50 volume percent of the clusters having a mean diameter that is at least 3 times the mean diameter of the ITO nanoparticles, and preferably at least 90 volume percent of the clusters having a mean diameter that is at least 5 times the mean diameter of the ITO nanoparticles. In one embodiment, these clusters may have a largest dimension of 50 nm-1 μm, preferably 75 nm-800 nm, more preferably 100-500 nm.

In one embodiment, the ITO nanoparticles are in the form of semispherical nanoparticles having diameters of 10-20 nm, preferably 12-19 nm, more preferably 14-18 nm and/or cubic nanoparticles having widths of 40-120 nm, preferably 60-100 nm, more preferably 65-90 nm. However, in some embodiments, semispherical nanoparticles may have diameters of smaller than 10 nm or greater than 20 nm, or cubic nanoparticles may have widths of smaller than 40 nm or greater than 120 nm. Semispherical nanoparticles may be spherical, ovoidal, pill-shaped, ellipsoid, or have some other rounded, convex shape. Preferably the distance from the centroid of a semispherical nanoparticle to any point on the surface is within 30% of the average distance, preferably within 20% of the average distance. Cubic nanoparticles may not necessarily be cubes, but preferably rectangular prisms that have dimensions (length, width, and height) within 40% of the average dimension, preferably within 30% of the average dimension. In other embodiments, ITO nanoparticles that are neither semispherical nor rectangular prisms may be used.

Preferably, in one embodiment, ITO nanoparticles in the form of semispherical nanoparticles have a uniform shape. Alternatively, the shape may be non-uniform. As used herein, the term "uniform" refers to an average consistent shape that differs by no more than 10%, by no more than 5%, by no more than 4%, by no more than 3%, by no more than 2%, by no more than 1% of the distribution of nanowires having a different shape. As used herein, the term "non-uniform" refers to an average consistent shape that differs by more than 10% of the distribution of semispherical nanoparticles having a different shape. In one embodiment, the shape is uniform and at least 90% of the nanoparticles are rounded or semispherical, and less than 10% are polygonal or substantially prismatic. In another embodiment, the shape is non-uniform and less than 90% of the nanoparticles are rounded or semispherical, and greater than 10% are polygonal or substantially prismatic. In one embodiment, the semispherical nanoparticles of the present disclosure are monodisperse, having a coefficient of variation or relative standard deviation, expressed as a percentage and defined as the ratio of the particle size standard deviation ($\sigma$) to the particle size mean ($\mu$) multiplied by 100, of less than 25%, preferably less than 10%, preferably less than 8%, preferably less than 6%, preferably less than 5%, preferably less than 4%, preferably less than 3%, preferably less than 2%. In a preferred embodiment, the semispherical nanoparticles of the present disclosure are monodisperse having a size distribution ranging from 80% of the average semispherical nanoparticle size to 120% of the average semispherical nanoparticle size, preferably 90-110%, preferably 95-105% of the average semispherical nanoparticle size.

Similarly, in one embodiment, ITO nanoparticles in the form of cubic nanoparticles have a uniform shape. Alternatively, the shape may be non-uniform. In one embodiment, the shape is uniform and at least 90% of the nanoparticles are cubic or substantially prismatic, and less than 10% are rounded or semispherical. In another embodiment, the shape is non-uniform and less than 90% of the nanoparticles are cubic or substantially prismatic and greater than 10% are rounded or semispherical. In one embodiment, the cubic nanoparticles of the present disclosure are monodisperse, having a coefficient of variation or relative standard deviation, expressed as a percentage and defined as the ratio of the particle size standard deviation ($\sigma$) to the particle size mean ($\mu$) multiplied by 100, of less than 25%, preferably less than 10%, preferably less than 8%, preferably less than 6%, preferably less than 5%, preferably less than 4%, preferably less than 3%, preferably less than 2%. In a preferred embodiment, the cubic nanoparticles of the present disclosure are monodisperse having a size distribution ranging from 80% of the average cubic nanoparticle size to 120% of the average cubic nanoparticle size, preferably 90-110%, preferably 95-105% of the average cubic nanoparticle size.

In one embodiment, where the ITO nanoparticles comprise both forms of cubic nanoparticles and semispherical nanoparticles, the mass ratio of cubic nanoparticle to semispherical nanoparticles may be 1:1,000-1,000:1, preferably 1:100-100:1, more preferably 1:10-10:1, even more preferably 1:5-5:1, or 1:2-2:1.

In an alternative embodiment, the ITONP electrode may be used in the field of batteries, fuel cells, photo-chemical cells, hydrogen sensors, semiconductors (such as field effect transistors), magnetic semiconductors, capacitors, data storage devices, biosensors (such as redox protein sensors), photovoltaics, liquid crystal screens, plasma screens, touch screens, OLEDs, antistatic deposits, optical coatings, reflective coverings, anti-reflection coatings, and/or reaction catalysis. Similarly, in one embodiment, the ITONP electrode may be coated with another material. For example, the ITONP electrode may be coated with a layer of gold. A gold-coated ITONP electrode may then be used for analyte detection using surface enhanced Raman scattering (SERS).

In one embodiment, the ITONP electrode does not comprise platinum, gold, graphite, and/or glassy carbon.

According to a second aspect, the present disclosure relates to a method for producing the ITONP-modified ITO electrode of the first aspect. This method involves reacting an ITO electrode with a solution comprising an alkoxysilane and an alcohol to produce the silanized ITO electrode, then contacting the silanized ITO electrode with an aqueous solution of ITO nanoparticles, and then drying to produce the ITONP-modified ITO electrode.

In one embodiment, before the step of reacting the ITO electrode with the solution, the ITO electrode may be cleaned, for example by sonication in methanol, ethanol, acetone, chloroform, or some other solvent. The ITO electrodes may then be sonicated in deionized or distilled water. The ITO electrodes may then be dried by an inert gas stream, a drying oven, a desiccator, a vacuum chamber, or may be left at room temperature to dry. The cleaned electrodes may be pretreated by contacting with an aqueous cleaning solution comprising 1-7 vol %, preferably 3-5 vol % $H_2O_2$ and 1-7 vol %, preferably 3-5 vol % $NH_4OH$, each relative to a total volume of the solution. The aqueous cleaning solution may be heated to 50-90° C., preferably 60-80° C., and the contacting may proceed for 0.5-2 h, preferably 1.25-1.75 h. The ITO electrodes may then be washed with water and dried. In other embodiments, other methods of pretreatment may be possible, such as exposure to oxygen plasma, UV radiation, or acidic oxidizing solutions (such as a mixture of sulfuric acid and hydrogen peroxide).

The ITO electrode is then reacted with the solution comprising the alkoxysilane and alcohol. In one embodiment, the solution comprises 0.5-4 vol %, preferably 1-3 vol %, more preferably 1.5-2.5 vol % of the alkoxysilane relative to a total volume of the solution. In one embodiment, the alkoxysilane may be (3-aminopropyl)-diethoxy-methylsilane (APDEMS), (3-aminopropyl)-dimethyl-ethoxysilane (APDMES), (3-aminopropyl)triethoxysilane (APTES), (3-aminopropyl)-trimethoxysilane (APTMS), (3-glycidoxypropyl)-dimethyl-ethoxysilane (GPMES), (3-mercaptopropyl)-trimethoxysilane (MPTMS), (3-mercaptopropyl)-methyl-dimethoxysilane (MPDMS), vinyltrimethoxysilane, chloropropyltrimethoxysilane, phenyltrimethoxysilane, cyanoethyltrimethoxysilane, p-tolyltrimethoxysilane, trifluoropropyltrimethoxysilane, nonafluorohexyltrimethoxysilane, octadecyltrichlorosilane, heptadecafluorodecyltrichlorosilane, heneicosafluorododecyltrichlorosilane, or some other alkoxysilane. However, in other embodiments, the solution may comprise less than 0.5 vol % alkoxysilane or greater than 4 vol % alkoxysilane. Preferably the alkoxysilane is an aminosilane, such as (3-aminopropyl)-diethoxy-methylsilane (APDEMS), (3-aminopropyl)-dim ethyl-ethoxy silane (APDMES), (3-aminopropyl)triethoxysilane (APTES), (3-aminopropyl)-trimethoxysilane (APTMS), or some other aminosilane. In a preferred embodiment, the alkoxysilane is (3-aminopropyl) trimethoxysilane (APTMS). The alcohol may be ethanol, methanol, isopropanol, butanol, ethylene glycol, propylene glycol, or some other alcohol and may be present in the solution at 96-99.5 vol %, preferably 97-99 vol %, more preferably 97.5-98.5 vol %, relative to a total volume of the solution. However, in some embodiments, the alcohol may be present in the solution volume percentage less than 96 vol % or greater than 99.5 vol %.

The solution may be dropped, sprayed, poured, spread, or spin coated on the surface of the ITO film of the ITO electrode, though in other embodiments, the ITO electrode may be momentarily dipped in the solution, or instead submerged in the solution for a period of time. Preferably the ITO electrode is submerged in the solution for a period of time, for instance, 6-24 h, preferably 10-16 h. The reaction of the solution with the ITO film produces a silanized ITO electrode. The silanized ITO electrode may then be washed with an alcohol such as ethanol, methanol, isopropanol, preferably ethanol, and then dried by any of the means described previously. Preferably, the silanized ITO electrode is dried under an argon or nitrogen gas stream.

Next, the silanized ITO electrode is contacted with an aqueous solution of ITO nanoparticles and dried again. In one embodiment, 150-650 μg of ITO nanoparticles are in the aqueous solution for every 1 $cm^2$ of silanized ITO electrode contacted. In one embodiment, the aqueous solution may comprise ITONPs at a concentration of 0.5-5 mg/mL, preferably 1-4 mg/mL, more preferably 1.5-2.5 mg/mL, though in some embodiments, the ITONPs may be in present at a concentration of less than 0.5 mg/mL or greater than 5 mg/mL. Preferably the aqueous solution has a pH of 7.6-9.0, preferably 8.0-8.5. The aqueous solution may have a volume of 80-500 preferably 100-400 more preferably 120-300 μL per every 1 $cm^2$ of silanized ITO electrode contacted, though in other embodiments, the aqueous solution may have a volume (μL) per area ($cm^2$) ratio of less than 80 μL/$cm^2$ or greater than 500 μL/$cm^2$.

Following the contacting, the silanized ITO electrode may be dried in an oven at 35-50° C., preferably 37-45° C., producing the ITONP electrode of the first aspect. Alternatively, after the contacting, the silanized ITO electrode may be dried in a desiccator, at atmospheric pressure or lower, or the silanized ITO electrode may be left at room temperature to dry.

In one embodiment, the silanized ITO electrode is contacted by dropping the aqueous solution onto the silanized ITO electrode. This method is considered to be essentially equivalent to dripping the aqueous solution or applying one or more droplets of the aqueous solution. For example, a droplet of the needed volume may be formed on the tip of a volumetric pipette, and then contacted to and left on the surface of the silanized ITO electrode.

In alternative embodiments, ITONPs may be deposited onto the silanized ITO electrode by electrodeposition, spin coating, dipping, or immersing the silanized ITO electrode into a solution of ITONPs. In other alternative embodiments, the formation of the ITONP electrode may involve lithography, more preferably nanolithography. For instance, nanolithography may be used to pattern the ITO film. Nanolithography techniques may be categorized as in series or parallel, mask or maskless/direct-write, top-down or bottom-up, beam or tip-based, resist-based or resist-less methods all of which are acceptable in terms of the present disclosure. Exemplary nanolithography techniques include, but are not limited to, optical lithography, photolithography, directed self-assembly, extreme ultraviolet lithography, electron beam lithography, electron beam direct write lithography, multiple electron beam lithography, nanoimprint lithography, step-and-flash imprint lithography, multiphoton lithography, scanning probe lithography, dip-pen nanolithography, thermochemical nanolithography, thermal scanning probe lithography, local oxidation nanolithography, molecular self-assembly, stencil lithography, X-ray lithography, laser printing of single nanoparticles, magnetolithography, nanosphere lithography, proton beam writing, charged particle lithography, ion projection lithography, electron projection lithography, neutral particle lithography and mixtures thereof. In another alternative embodiment, the ITONP electrode may be formed by a sol-gel or chemical vapor deposition method. In another alternative embodiment, the ITONP may be synthesized by two or more techniques, for instance, a nanolithography method and then an electrodeposition method.

In an alternative embodiment, ITO nanoparticles may be silanized by a similar reaction, and then contacted with and dried on a non-silanized ITO electrode or a silanized ITO electrode.

In one embodiment, the method does not comprise an annealing step. The ITO electrode is not annealed before or after silanization, and the silanized ITO electrode is not annealed before or after contacting with the aqueous solution of ITO nanoparticles. For example, the entire method of making the ITONP electrode from the ITO electrode as described by the second aspect of the disclosure may be performed at temperatures no greater than 80° C., preferably no greater than 72° C. In a further embodiment, the method may be carried out entirely at room temperature (i.e., 20-30° C., preferably 22-27° C.). In an alternative embodiment, however, the ITONP electrode may be annealed.

Characterization may be used to establish understanding and control of the ITO film, the silanized ITO film, the ITO nanoparticles, and/or the ITONP electrode. In one embodiment, it is envisioned that characterization is done using a variety of techniques. Exemplary techniques include, but are not limited to, electron microscopy (TEM, SEM, FESEM), atomic force microscopy (AFM), ultraviolet-visible spectroscopy (UV-Vis), dynamic light scattering (DLS), X-ray photoelectron spectroscopy (XPS), X-ray fluorescence (XRF), powder X-ray diffraction (XRD), energy dispersive X-ray spectroscopy (EDX), thermogravimetric analysis (TGA), Fourier transform infrared spectroscopy (FTIR), matrix-assisted laser desorption/ionization time-of-flight mass spectrometry (MALDI-TOF), Rutherford backscattering spectrometry (RBS), dual polarization interferometry, time-of-flight secondary ion mass spectrometry (ToF-SIMS), electron energy loss spectroscopy (EELS), high-angle annular dark field (HAADF), near infrared (NIR) spectroscopy, nuclear magnetic resonance (NMR), or combinations thereof.

According to a third aspect, the present disclosure relates to an electrolytic cell. The electrolytic cell has a working electrode comprising the ITONP-modified ITO electrode of the first aspect in contact with an electrolyte solution. The electrolytic cell also has a counter electrode in contact with the electrolyte solution. The electrolyte solution comprises 0.1 μM-10 mM, preferably 0.5 μM-1 mM, more preferably 1 μM-500 μM aqueous sulfide ($^-SH$, $S^{2-}$, and/or $H_2S$). In one embodiment, the electrolyte solution has a pH of 6.0-8.0, preferably 6.5-7.5, more preferably 6.8-7.2. In an alternative embodiment, the electrolyte solution does not comprise aqueous sulfide.

In one embodiment, the counter electrode comprises gold, platinum, or carbon. In a further embodiment, the counter electrode comprises platinum. In one embodiment, the counter electrode may be in the form of a wire, a rod, a cylinder, a tube, a scroll, a sheet, a piece of foil, a woven mesh, a perforated sheet, or a brush. The counter electrode may be polished in order to reduce surface roughness or may be texturized with grooves, channels, divots, microstructures, or nanostructures.

In another further embodiment, where the counter electrode comprises platinum, the counter electrode is in the form of a rod or wire. Alternatively, the counter electrode may comprise some other electrically-conductive material such as platinum-iridium alloy, iridium, titanium, titanium alloy, stainless steel, gold, cobalt alloy, and/or some other electrically-conductive material.

In a preferred embodiment, the counter electrode has at least one outer surface comprising an essentially inert, electrically conducting chemical substance, such as platinum, gold, or carbon. In another embodiment, the counter electrode may comprise solid platinum, gold, or carbon. The form of the counter electrode may be generally relevant only in that it needs to supply sufficient current to the electrolyte solution to support the detection of aqueous sulfide. The material of the counter electrode should thus be sufficiently inert to withstand the chemical conditions in the electrolyte solution, such as acidic or basic pH values, without substantial fouling or degradation. The counter electrode preferably should not leach out any chemical substance that interferes with the sulfide detection process or might lead to undesirable contamination of the ITONP electrode.

In one embodiment, the counter electrode is in the form of a rod or wire. The rod or wire may have straight sides and a circular cross-section, similar to a cylinder. A ratio of the length of the rod or wire to its width may be 1,500:1-1:1, preferably 500:1-2:1, more preferably 300:1-3:1, even more preferably 200:1-4:1. The length of the rod or wire may be 0.5-50 cm, preferably 1-30 cm, more preferably 3-20 cm, and a long wire may be coiled or bent into a shape that allows the entire wire to fit into an electrochemical cell. The diameter of the rod or wire may be 0.5-20 mm, preferably 0.8-8 mm, more preferably 1-3 mm. In some embodiments, a rod may have an elongated cross-section, similar to a ribbon or strip of metal.

Preferably, to maintain uniform concentrations and/or temperatures of the electrolyte solution, the electrolyte solution may be stirred or agitated when a potential is applied to the electrodes of the electrolytic cell. The stirring or agitating may be done intermittently or continuously. This stirring or agitating may be by a magnetic stir bar, a stirring rod, an impeller, a shaking platform, a pump, a sonicator, a gas bubbler, or some other device. Preferably the stirring is done by an impeller or a magnetic stir bar. Preferably the electrolyte solution is maintained at a temperature of 20-27° C., more preferably 22-26° C.

In one embodiment, the electrolytic cell is a vessel having an internal cavity for holding the electrolyte solution. The vessel may be cylindrical, cuboid, frustoconical, spherical, or some other shape. The vessel walls may comprise a material including, but not limited to, glass, polypropylene, polyvinyl chloride, polyethylene, and/or polytetrafluoroethylene, and the vessel walls may have a thickness of 0.1-3 cm, preferably 0.1-2 cm, more preferably 0.2-1.5 cm. The internal cavity may have a volume of 2 mL-100 mL, preferably 2.5 mL-50 mL, more preferably 3 mL-20 mL. In another embodiment, a volume smaller than 2 mL maybe used, for instance, in a microfluidic application.

In one embodiment, the electrolyte solution further comprises an inorganic salt at a concentration of 10 mM-1 M, preferably 25 mM-200 mM, more preferably 35 mM-70 mM. However, in some embodiments, the inorganic salt may be present at a concentration of less than 10 mM or greater than 1 M. The inorganic salt may be NaCl, KCl, LiCl, NaBr, KBr, LiBr, $NaNO_3$, $KNO_3$, $LiNO_3$, or some other inorganic salt. Preferably the inorganic salt is $KNO_3$.

In a further embodiment, the electrolyte solution comprising an inorganic salt further comprises a buffer at a concentration of 5-500 mM, preferably 15-100 mM, more preferably 20-75 mM. However, in some embodiments, the buffer may be present at a concentration of less than 5 mM or greater than 500 mM. The buffer may be tris (tris (hydroxymethyl)aminomethane), HEPES (4-(2-hydroxyethyl)-1-piperazineethanesulfonic acid), CAPS (N-cyclohexyl-3-aminopropanesulfonic acid), tricine (N-(tri (hydroxymethyl)methyl)glycine), or some other buffer. Preferably the buffer is tris.

In one embodiment, an electric potential may be applied to the electrodes by a battery, such as a battery comprising one or more electrochemical cells of alkaline, lithium, lithium-ion, nickel-cadmium, nickel metal hydride, zinc-air, silver oxide, and/or carbon-zinc. In another embodiment, the potential may be applied through a potentiostat or some other source of direct current, such as a photovoltaic cell. In one embodiment, a potentiostat may be powered by an AC adaptor, which is plugged into a standard building or home electric utility line. In one embodiment, the potentiostat may connect with a reference electrode in the electrolyte solution. Preferably the potentiostat is able to supply a relatively stable voltage. For example, in one embodiment, the electrolytic cell is subjected to a voltage that does not vary by more than 5%, preferably by no more than 3%, preferably by no more than 1.5% of an average value throughout the subjecting. In another embodiment, the voltage may be modulated, such as being increased or decreased linearly, being applied as pulses, or being applied with an alternating current.

In one embodiment, the electrolytic cell further comprises a reference electrode in contact with the electrolyte solution. A reference electrode is an electrode which has a stable and well-known electrode potential. The high stability of the electrode potential is usually reached by employing a redox system with constant (buffered or saturated) concentrations of each relevant species of the redox reaction. A reference electrode may enable a potentiostat to deliver a stable voltage to the working electrode or the counter electrode. The reference electrode may be a standard hydrogen electrode (SHE), a normal hydrogen electrode (NHE), a reversible hydrogen electrode (RHE), a saturated calomel electrode (SCE), a copper-copper(II) sulfate electrode (CSE), a silver chloride electrode (Ag/AgCl), a pH-electrode, a palladium-hydrogen electrode, a dynamic hydrogen electrode (DHE), a mercury-mercurous sulfate electrode, or some other type of electrode. In a preferred embodiment, a reference electrode is present and is a Ag/AgCl electrode. However, in some embodiments, the electrolytic cell does not comprise a third electrode.

In one embodiment, the electrolytic cell has an aqueous sulfide limit of detection of 1-5 µM, preferably 2-4 µM for an amperometric measurement of the electrolyte solution. However, in some embodiments, the limit of detection may be less than 1 µM or greater than 5 µM. An amperometric measurement may be performed by monitoring the flow of current at a fixed voltage, such as a voltage of 10 mV-1 V, preferably 100 mV-500 mV, more preferably 200 mV-400 mV. The oxidation of the aqueous sulfide into $S^0$ and/or $SO_3^{2-}$ may cause an increase in current, and the current (which is a measure of charge/time) may be integrated over time to find the amount of charge needed to oxidize the aqueous sulfide. Preferably, the initial concentration of the aqueous sulfide has a linear relationship with this amount of charge. A greater concentration produces a greater charge. Preferably, an unknown concentration may be determined by constructing a standard calibration curve.

In one embodiment, the electrolytic cell has an aqueous sulfide limit of detection of 0.5-1.4 µM, preferably 0.7-1.2 µM, more preferably 0.8-1.0 µM for a chronocoulometric measurement of the electrolyte solution. However, in some embodiments, the limit of detection may be less than 0.5 µM or greater than 1.4 µM. A chronocoulometric measurement may be performed by monitoring the amount of charge that flows through the electrolytic cell over time, due to the oxidation of the aqueous sulfide into $S^0$ and/or $SO_3^{2-}$. Preferably, when compared with the same potential and at the same time point, the amount of charge has a linear relationship with the initial concentration. In one embodiment, the potential may be a fixed voltage, such as a voltage of 10 mV-1 V, preferably 100 mV-500 mV, more preferably 200 mV-400 mV. The time point of measurement may be 20-180 s, preferably 60-150 s, more preferably 90-130 s following the initial application of the potential. A calibration curve may be produced from these measurements. However, in some embodiments, lower concentrations of aqueous sulfide (for example, less than 50 or less than 30 µM) may produce a different linear behavior than greater concentrations (i.e. different slopes and/or y-axis intercepts). This difference may result from different ratios of $S^0$ to $SO_3^{2-}$ produced when aqueous sulfide is oxidized.

In one embodiment, the electrolytic cell has a reproducible chronocoulometric measurement for five or more, preferably seven or more electrolyte solutions having substantially similar aqueous sulfide concentrations. As defined here, the electrolyte solutions having substantially similar aqueous sulfide concentrations means that each solution has an aqueous sulfide concentration that is within 2%, preferably within 1% of the average aqueous sulfide concentration. The chronocoulometric measurement being reproducible means that across each measurement time period while applying identical parameters, the charge of the electrolytic cell a certain time point varies by 10% or less, preferably 5% or less, more preferably 2% or less than the average charge at that time point. In this embodiment, the same ITONP electrode is used with the five or more electrolyte solutions.

In a further embodiment, the five or more electrolyte solutions have an aqueous sulfide concentration of 10-500 preferably 20-300 more preferably 50-150 µM.

In an alternative embodiment, the electrolytic cell may detect aqueous sulfide through cyclic voltammetry, pulse voltammetry, double potential step chronocoulometry, or though some other electrochemical process.

Figure 7:
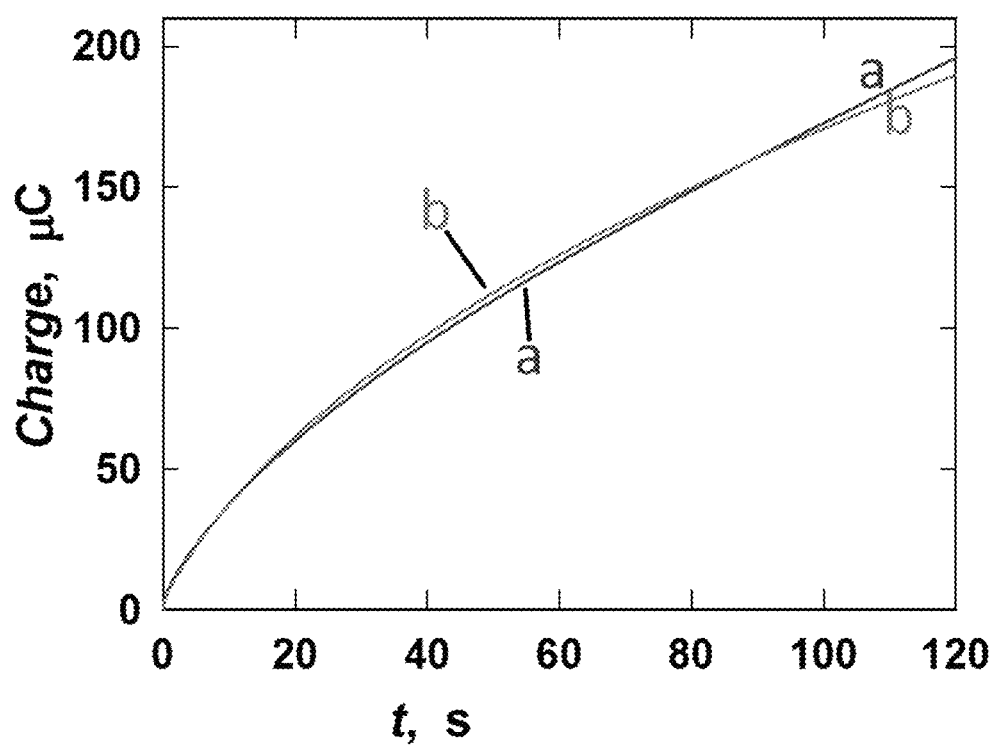
FIG. 7 shows the chronocoulogram of an ITONP-modified ITO electrode (produced by drop-drying), in 25 mM Tris buffer, 50 mM $KNO_3$, and 100 μM $Na_2S$ at pH 8 and 0.3 V, in the absence (a) and presence (b) of 100 μM each of sulfite, sulfate, chloride, carbonate, acetate, citrate, oxalate, elemental sulfur, benzene, toluene, and xylene.

In one embodiment, a chronocoulometric measurement of the electrolytic cell is substantially similar to a second chronocoulometric measurement of an otherwise identical second electrolytic cell further comprising at least one interferent in a second electrolyte solution. As defined here, the chronocoulometric measurement being substantially similar to a second chronocoulometric measurement means that across the measurement time period while applying identical parameters, the charges between the two measurements vary by 10% or less, preferably 5% or less, more preferably 2% or less. This embodiment is shown in FIG. 7, where (a) is a chronocoulometric measurement of an electrolytic cell with 100 µM sulfide and without interferents, and (b) is a second chronocoulometric measurement of a second electrolytic cell comprising 100 µM sulfide and 100 µM each of sulfite, sulfate, chloride, carbonate, acetate, citrate, oxalate, elemental sulfur, benzene, toluene, and xylene. As defined here, the interferent is a compound whose presence is known to cause interference with general analytical procedures for detecting sulfide, where this interference generates incorrect results. Here, the interferent is at least one selected from the group consisting of sulfite, sulfate, chloride, carbonate, acetate, citrate, oxalate, elemental sulfur, benzene, toluene, and xylene. Preferably the interferent is at least one selected from the group consisting of sulfite, sulfate, chloride, carbonate, acetate, citrate, oxalate, and elemental sulfur. Even more preferably, the interferent is at least one selected from the group consisting of sulfite, sulfate, and elemental sulfur. In one embodiment, one or more interferents may be present in the second electrolyte solution at individual concentrations that are within 20%, preferably within 10% of the sulfide concentration. In other embodiments, the interferent may be present at a concentration of up to 12 times, preferably up to 15 times, more preferably up to 20 times the concentration of the sulfide. However, in some embodiments, the concentration of the interferent may be less than the concentration of the sulfide.

In one embodiment, the aqueous sulfide originates from hydrogen sulfide gas. For example, a gas sample comprising hydrogen sulfide may be bubbled into or exposed to the electrolyte solution to produce aqueous sulfide. In another embodiment, the hydrogen sulfide may be adsorbed to a solid support, which is then washed with or submerged into the electrolyte solution. In one embodiment, fixed concentrations of hydrogen sulfide gas may be used to construct a calibration curve, and the electrolytic cell may be able to determine a concentration of hydrogen sulfide gas in an environment or a gas sample.

In a further embodiment, the hydrogen sulfide gas is produced by at least one selected from the group consisting of petroleum extraction, petroleum refinement, natural gas extraction, natural gas refinement, fuel combustion, waste water treatment, tanneries, paper mills, and textile manufacturing. Hydrogen sulfide gas may also be detected in petroleum or natural gas transportation, in residences, in food processing facilities, in chemical plants, and in other places.

The examples below are intended to further illustrate protocols for preparing and characterizing the ITONP electrode, and uses thereof, and are not intended to limit the scope of the claims [M. A. Aziz et al. *Electroanalysis*, 2017, 29, 1683-1690—incorporated herein by reference in its entirety].

EXAMPLE 1

Reagents

ITO (30 Ω/sq) electrodes were purchased from Geomatec, Japan. Sodium sulfide ($Na_2S$) nonahydrate, sodium sulfite ($Na_2SO_3$), sodium sulfate ($Na_2SO_4$), sulfur (S), sodium chloride (NaCl), sodium carbonate ($Na_2CO_3$), sodium acetate ($CH_3COONa$), sodium citrate dihydrate, sodium oxalate, potassium nitrate ($KNO_3$), benzene, toluene, xylene, Trizma base (Tris), concentrated hydrochloric acid, colloidal 18 nm ITO nanoparticles (ITONPs, 20 wt % in $H_2O$), and (3-aminopropyl) trimethoxysilane (APTMS) were obtained from Sigma-Aldrich Co. Ltd. The compositions of both the ITONPs and the ITO electrode were 90% $In_2O_3$ and 10% $SnO_2$. Ethanol was purchased from Carlo Erba Reagents, France. De-ionized water was used to make all solutions used in the experiments, and was obtained using a water purification system (Barnstead Nanopure, Thermo Scientific, 7148, USA).

EXAMPLE 2

Preparation of the ITONP-Modified ITO Electrode

The ITO substrates were ultrasonically cleaned in ethanol and then in de-ionized water for 5 min for each cleaning cycle, followed by drying at room temperature (RT). The cleaned electrodes were pretreated in a mixture of 5:1:1 $H_2O/H_2O_2$ (30%)/$NH_4OH$ (30%) (v/v/v) at 70° C. for 1.5 h. After washing with water and drying at RT, the pretreated ITO substrates were then immersed in ethanol containing 2% (v/v) APTMS for 12 h to obtain APTMS/ITO. After washing with ethanol, the modified electrodes were dried under a nitrogen stream. Finally, a volume of 50 µL of an aqueous solution of ITONPs (2 mg/mL) was dropped onto the APTMS/ITO electrode and dried at 40° C. Different methods for preparing the ITONP-modified ITO electrode were also tested, as described in later examples.

EXAMPLE 3

Instrumentation

The pH values of the buffer solutions were recorded using a dual channel pH meter (XL60, Fisher Scientific). All electrochemical measurements were performed using a CHI (760E) electrochemical workstation (CH Instruments, Austin, Tex.). Bare ITO and modified ITO were used as the working electrodes, Ag/AgCl was used as the reference electrode, and a platinum wire was used as the counter electrode. All electrochemical experiments were carried out at RT without deaeration. Images were obtained by using a field emission scanning electron microscope (FE-SEM, TESCAN LYRA 3, Czech Republic), and by using a transmission electron microscope (TEM, JEOL, JEM 2011) operated at 200 kV and equipped with a 4 k×4 k CCD camera (Ultra Scan 400SP, Gatan).

EXAMPLE 4

Preparation and Morphological Characterization of the ITONP-Modified ITO Electrode FIGS. 1A and B shows TEM images of the ITONPs that were used to modify the ITO electrodes. These images clearly show the presence of semispherical NPs along with some cubic NPs. The average size of the semispherical particles was measured to be about 18 nm, as indicated by Sigma-Aldrich. However, the cubic particles were observed to be considerably larger, with dimensions of about 60-100 nm.

Four methods to immobilize ITONPs on the ITO electrode surfaces were tested: (i) drop-drying of a 2 mg/mL ITONP solution (aq.) on a bare ITO electrode, (ii) electrochemical anodic deposition on bare ITO from an aqueous solution of both 2 mg/mL of ITONPs and 2 mg/mL sodium oxalate, (iii) dipping an APTMS-functionalized ITO substrate (APTMS/ITO) in an aqueous 2 mg/mL ITONP solution, and (iv) drop-drying a 2 mg/mL ITONP solution (aq.) onto an APTMS-functionalized ITO substrate (APTMS/ITO).

In the first method, a homogeneous film was not obtained as ITONPs aggregated in certain areas on the electrode.

In the second method, various positive potentials (from 0.6 to 2.5 V, vs. AgCl) were applied to deposit ITONPs from an aqueous solution of 2 mg/mL ITONPs and 2 mg/mL sodium oxalate. ITONPs could not be deposited by this method even though other materials, such as $IrO_x$, may be deposited under similar deposition conditions [H. A. Elsen, et al. *Journal of The Electrochemical Society,* 2009, 156, F1-F6—incorporated herein by reference in its entirety].

In the third method, ITO nanoparticles were deposited as a sub-monolayer (FESEM data not shown). However, in this method, all of the ITONPs were found in the aggregated state (cluster type). Interestingly, the aggregated NPs (cluster type) were distributed homogeneously throughout the surface (no aggregation occurred in certain areas). The modified electrode prepared using this method is denoted as ITONP(dip-washing)/APTMS/ITO. The cause of the aggregation (cluster formation) is not completely understood. Without being bound by any particular hypothesis, the ITONPs may have formed in an aggregated state while in the colloidal solution. The nature of the binding force between the ITONPs and APTMS/ITO is also not entirely clear. APTMS-functionalized surfaces have amine-terminated functional groups, and the pKa values of such amine-functionalized surfaces have been measured to be in the range 3.9-7.6 [D. V. Vezenov, et al. *J. Am. Chem. Soc.* 1997, 119, 2006-2015; T. Z. Mengistu, et al. *Langmuir,* 2006, 22, 5301-5307; P. Abiman, et al. *Chem. Eur. J.,* 2007, 13, 9663-9667—each incorporated herein by reference in its entirety]. This indicates that the amine group of the APTMS/ITO would not be protonated at pH 8.2, which is the pH of the used 2 mg/mL ITONP solution (aq). In contrast, the isoelectric point of ITO has been measured to be 8.68 [M. A. Aziz, et al. *Electroanalysis,* 2015, 27, 1268-1275—incorporated herein by reference in its entirety], and ITONPs would thus be positively charged at pH 8.2; that is, there is no possibility of electrostatic binding between the amine functionalized surface and ITONP. Thus, the binding between ITONPs and the APTMS/ITO surfaces could be covalent bonding or physical entrapment.

Figure 2E:
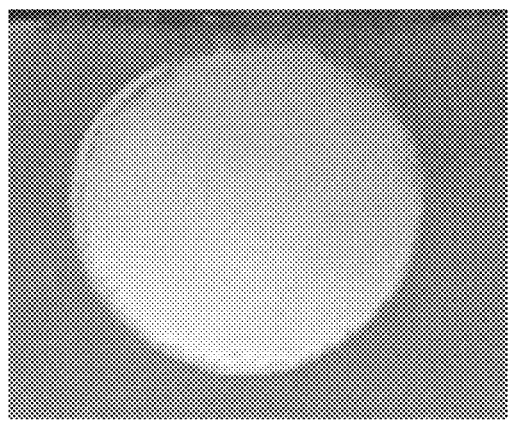
FIG. 2E is an image of the ITONP electrode showing the even distribution of the ITONP on the surface.

In the fourth method, a very homogeneous film was obtained according to observations with the naked eye (FIG. 2E). Around 0.3 $cm^2$ of the surface may be covered by dropping 50 µL of a 2 mg/mL aqueous solution. This preparation was reproducible. The bare ITO surface was observed to be smooth (FIGS. 2A and 2B). The ITONP/APTMS/ITO surface shows the presence of semispherical NPs along with some cubic NPs (FIGS. 2C and 2D). These data are consistent with the TEM analysis. The modified electrode prepared by this method is denoted as ITONP (drop-drying)/APTMS/ITO. Comparing the results of the first method to the fourth method suggests that APTMS functionalization has a considerable role in the formation of a homogeneous ITONP-modified ITO surface.

EXAMPLE 5

Electrocatalytic Properties

FIGS. 3A-3D show cyclic voltammograms (CVs) of bare and modified ITO electrodes in 0.1 M $KNO_3$ in the absence (curves a) and presence (curves b) of 1 mM $Na_2S$. For the bare ITO electrode, sulfide ions started to oxidize at about 0 V, according to curve b in FIG. 3A, and a peak appeared at 0.7 V. This peak position differed from that reported earlier, being shifted to a more positive direction, due to a combined effect of using a higher concentration of sulfide ion (1 mM, rather than 0.1 mM) and a higher scan rate (50 mV/s, rather than 10 mV/s) [M. A. Aziz, et al. *Electroanalysis,* 2015, 27, 1268-1275—incorporated herein by reference in its entirety]. Note that this previous report also showed the peak position shifted in the positive direction as the concentration of sulfide was increased. For a quick and convenient analysis, 1 mM $Na_2S$ and a 50 mV/s scan rate were used in this study. In the previous report, the obtained limit of detection was 8.0 µM, higher than what would be desired for sensitive detection in a practical scenario. Therefore, the ITO electrode was modified to improve the sensitivity.

Figure 3A:
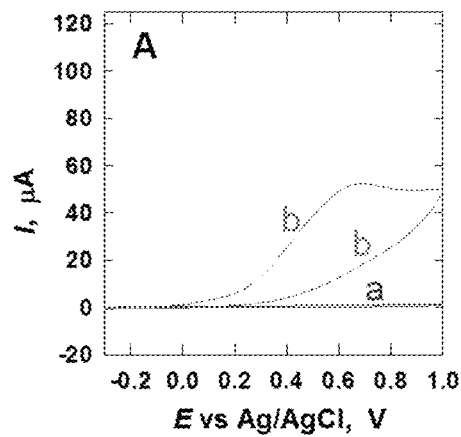
FIG. 3A is a cyclic voltammogram of a bare ITO electrode in the absence (a) and presence (b) of 1 mM $Na_2S$.
Figure 3B:
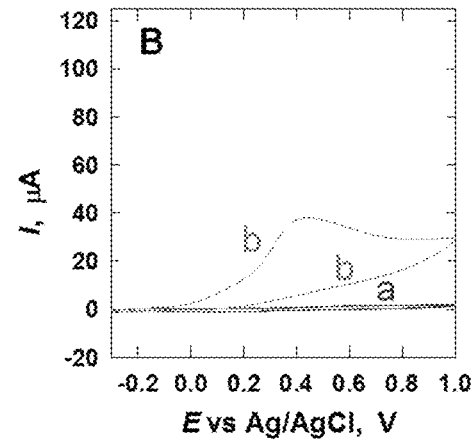
FIG. 3B is a cyclic voltammogram of a silanized ITO electrode in the absence (a) and presence (b) of 1 mM $Na_2S$.

According to FIG. 3B, the oxidation of sulfide at the APTMS/ITO electrode started at −0.1 V, which was 100 mV lower than that for the bare ITO electrode. Moreover, the sulfide ion oxidation peak at APTMS/ITO appeared at 0.4 V, which was 300 mV lower than that for the bare ITO electrode (FIGS. 3A and 3B). However, the sulfide oxidation peak current decreased upon modifying ITO with APTMS (see curve "b" in FIGS. 3A and 3B). Without being bound by any particular hypothesis, the decrease in the electro-oxidation potential of the ITO electrode upon being modified with APTMS may be due to the binding of the negatively charged sulfide ion to the positively charged $NH_3^+$ from the aqueous solution of 1 mM $Na_2S$ and 0.1 M $KNO_3$. Attached electroactive molecules on electrode surfaces are known to oxidize at lower potentials than do molecules in bulk solution. The decrease of the sulfide electro-oxidation signal upon APTMS functionalization may have been due to the electrocatalytic surfaces of ITO having been partially covered with APTMS.

Figure 3C:
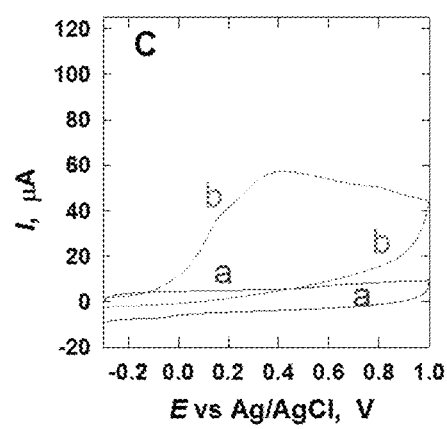
FIG. 3C is a cyclic voltammogram of an ITONP-modified ITO electrode (produced by dip-washing) in the absence (a) and presence (b) of 1 mM $Na_2S$.
Figure 3D:
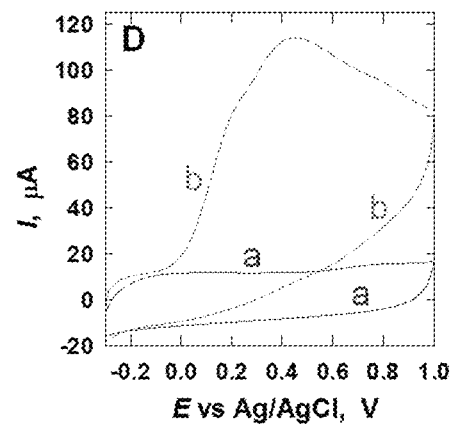
FIG. 3D is a cyclic voltammogram of an ITONP-modified ITO electrode (produced by drop-drying) in the absence (a) and presence (b) of 1 mM $Na_2S$.

The partial modification of APTMS/ITO with ITONPs increased the sulfide electro-oxidation peak current while maintaining the electro-oxidation potential at 0.4 V (curve "b" in FIG. 3C). This enhancement of the electro-oxidation signal was indicative of the electrocatalytic properties of the ITONPs toward sulfide electro-oxidation. The obtained sulfide electro-oxidation peak current with the ITONP(dip-washing)/APTMS/ITO electrode was similar to that obtained with the bare ITO electrode. To make a sensitive and selective sensor, the sulfide electro-oxidation current may be increased, while maintaining the low electro-oxidation potentials.

To enhance the sulfide electro-oxidation signal, more ITONPs were loaded on the APTMS surfaces by using the drop-drying method as described above. This ITONP(drop-drying)/APTMS/ITO electrode (curve "b" in FIG. 3D) showed a significantly improved sulfide electro-oxidation signal than did the ITONP(dip-washing)/APTMS/ITO electrode (curve "b" in FIG. 3C). The loading amount of ITONP in ITONP(drop-drying)/APTMS/ITO electrode is higher than that in ITONP(dip-washing)/APTMS/ITO. However, both electrodes produced current at a similar range of sulfide electro-oxidation potentials. Considering both electro-oxidation potential and current, the ITONP(drop-drying)/APTMS/ITO electrode was identified as the best candidate for sulfide electro-oxidation, and was considered for further study.

EXAMPLE 6

Figure 4A:
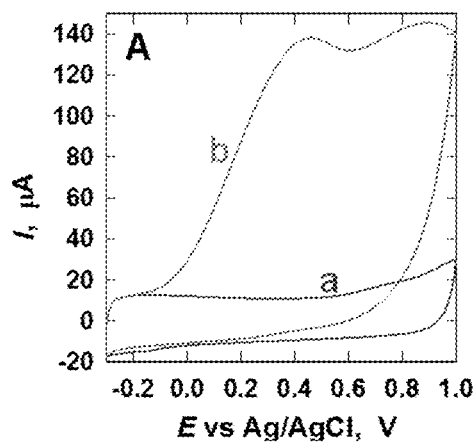
FIG. 4A is a cyclic voltammogram of an ITONP-modified ITO electrode (produced by drop-drying), in 50 mM Tris buffer at pH 7, in the absence (a) and presence (b) of 1 mM $Na_2S$.
Figure 4B:
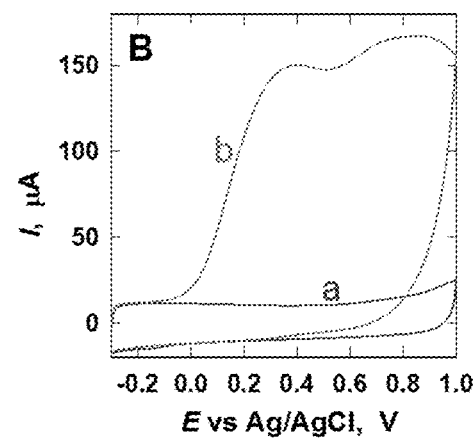
FIG. 4B is a cyclic voltammogram of an ITONP-modified ITO electrode (produced by drop-drying), in 25 mM Tris buffer and 50 mM $KNO_3$ at pH 7, in the absence (a) and presence (b) of 1 mM $Na_2S$.
Figure 4C:
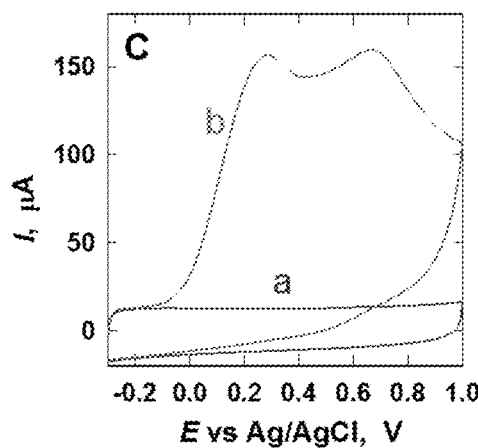
FIG. 4C is a cyclic voltammogram of an ITONP-modified ITO electrode (produced by drop-drying), in 25 mM Tris buffer and 50 mM $KNO_3$ at pH 8, in the absence (a) and presence (b) of 1 mM $Na_2S$.
Figure 4D:
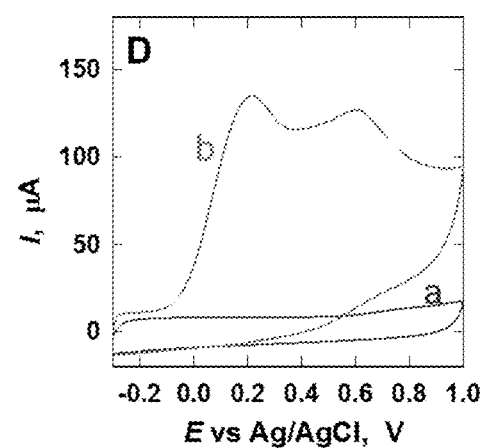
FIG. 4D is a cyclic voltammogram of an ITONP-modified ITO electrode (produced by drop-drying), in 25 mM Tris buffer and 50 mM $KNO_3$ at pH 9, in the absence (a) and presence (b) of 1 mM $Na_2S$.

Effect of the Inert Electrolyte and pH on Sulfide Electro-Oxidation using ITONP (Drop-Drying)/APTMS/ITO In the previous examples, 0.1 M $KNO_3$ was used as the inert electrolyte (pH 6.5). However, the pH of an aqueous solution of 0.1 M $KNO_3$ may be unintentionally varied quite a bit by the introduction, even in very small amounts, of pH-sensitive impurities, which would disrupt an accurate determination of the concentration of $Na_2S$. Therefore, 50 mM Tris buffer (pH 7) was used as the inert electrolyte in the next trial. As seen by comparing both "a" and "b" curves in FIG. 4A, the ITONP(drop-drying)/APTMS/ITO showed a high sulfide electro-oxidation current in the 50 mM Tris buffer (pH 7), with two distinct peaks at 0.45 V and 0.90 V. The sulfide electro-oxidation current obtained using the 50 mM Tris buffer (curve "b" in FIG. 4A) was higher than that obtained using 0.1 M $KNO_3$ (curve "b" in FIG. 3D). The first peak may have resulted from the oxidation of $^-SH$ to elemental sulfur ($S^0$), and the second peak may have been due to the further oxidation of the generated elemental $S^0$ to sulfite ions ($SO_3^{2-}$). In the next trial, sulfide was oxidized in an aqueous solution consisting of 50 mM $KNO_3$ and 25 mM Tris buffer (pH 7) (FIG. 4B) (this aqueous solution was made by mixing equal volumes of 0.1 M $KNO_3$ and 50 mM Tris buffer at pH 7). This mixed electrolyte solution (curve "b" in FIG. 4B) yielded a significantly higher sulfide electro-oxidation current at the ITONP(drop-drying)/APTMS/ITO electrode than did either 0.1 1M $KNO_3$ (curve "b" in FIG. 3D) or only 50 mM Tris buffer (curve "b" in FIG. 4A). This mixed electrolyte also showed two distinct sulfide electro-oxidation peaks, at 0.38 and 0.88 V, which were lower than that obtained in 50 mM Tris buffer (pH 7). As a result, a pH dependence study was performed using this mixed inert electrolyte (FIGS. 4B-4D). The obtained peak positions and peak currents at different pH values are summarized in Table 1.

TABLE 1

Peak potential ($E_p$) and peak current ($I_p$) values at the ITONP(drop-drying)/APTMS/ITO electrode of 1 mM sulfide in aqueous solutions made by mixing equal volumes of 0.1M $KNO_3$ and 50 mM Tris buffer at pH 7, pH 8, and pH 9.

| pH | $E_{p1}$ (V) | $E_{p1}$ (V) | $I_{p1}$ (μA) | $I_{p2}$ (μA) |
|---|---|---|---|---|
| 7 | 0.38 | 0.88 | 150 | 160 |
| 8 | 0.24 | 0.64 | 155 | 155 |
| 9 | 0.20 | 0.60 | 145 | 130 |

The positions of both sulfide electro-oxidation peaks were observed to shift to the negative direction as the pH was increased (Table 1). Lowering the electro-oxidation peak potential and increasing the current of any analyte improves the selectivity and sensitivity of detecting the analyte. Therefore, improved peak current on the first peak potential ($E_{P1}$) was sought rather than the second one ($E_{P2}$), as $E_{p1}$ is much lower than $E_{p2}$. A pH of 8 was found to yield the highest $I_{p1}$ with an acceptable $E_{p1}$ for fabricating a sensitive and selective electrochemical sensor. Such a high current was obtained because at this pH there were likely many $^-SH$ ions in solution [M. K. Amosa, et al. *NAFTA*, 2010, 61, 85-92; E. Bitziou, et al. *Anal. Chem.* 2014, 86, 10834-10840—each incorporated herein by reference in its entirety] and many positively charged species on the surface of the electrode, considering the 8.68 value of the isoelectric point of the ITO surface [M. A. Aziz, et al. *Electroanalysis*, 2015, 27, 1268-1275—incorporated herein by reference in its entirety]. Consequently, $^-SH$ ions may be easily adsorbed onto ITONP (drop-drying)/APTMS/ITO from an aqueous sulfide solution with a pH of 8. The adsorbed $^-SH$ ions would oxidize easily as explained above in reference to FIG. 3B. The 25 mM Tris buffer containing 50 mM $KNO_3$ and a pH of 8 was chosen as the preferred inert electrolyte.

EXAMPLE 7

Reproducibility of the Preparation of ITONP(Drop-Drying)/APTMS/ITO.

The reproducibility of the preparation of the ITONP(drop-drying)/APTMS/ITO electrode was tested by measuring the CVs of five different such electrodes in an aqueous solution made by mixing equal volumes of 0.1 M $KNO_3$ and 50 mM Tris buffer containing 1 mM sulfide. The recorded CVs from these five electrodes were similar, indicating the good reproducibility of the electrode preparation. As a result, ITONP (drop-drying)/APTMS/ITO was considered as a good candidate for sulfide electroanalysis.

EXAMPLE 8

Amperometric Determination of Sulfide Concentration.

Figure 5C:
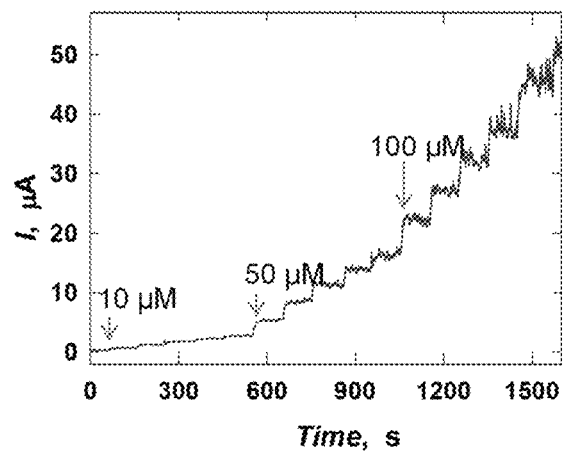
FIG. 5C is the corresponding calibration plot from the amperogram of FIG. 5A.
Figure 5C:
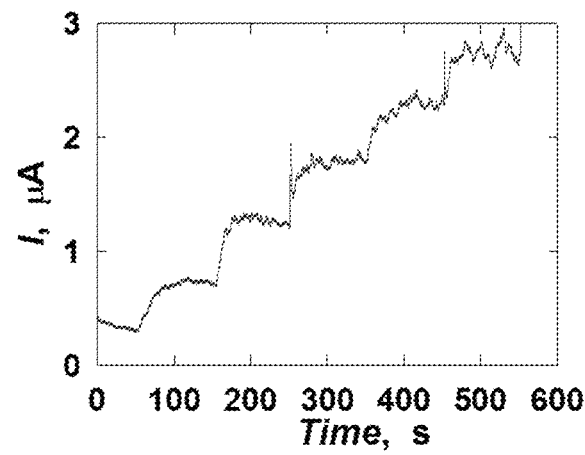
Figure 5C:
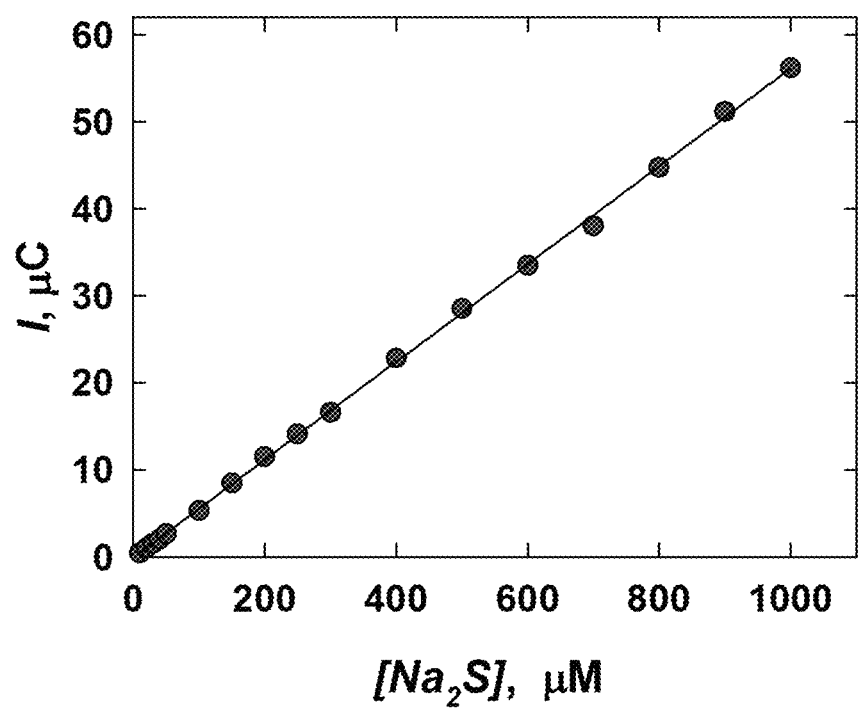

Based on the voltammetric experimental results, amperometric experiments were carried out to estimate the limit of detection and sensitivity of the ITONP(drop-drying)/APTMS/ITO-based sensor to sulfide in 25 mM Tris buffer containing 50 mM $KNO_3$ (pH 8). FIG. 5 shows a typical amperometric response of the ITONP(drop-drying)/APTMS/ITO-based sensor at 0.3 V upon successive addition of different concentrations of sulfide as marked. ITONP (drop-drying)/APTMS/ITO yielded a well-defined and sensitive signal for each addition of sulfide in the range of 10-1000 μM (FIG. 5A), whereas bare ITO resulted in a poor signal under the same experimental condition (data not shown). The relationship between the response current (after subtracting the mean of the zero sulfide response) and the sulfide concentration was found to be linear over the range 10-1000 μM (FIG. 5B) and to follow the linear regression equation y=0.0562x−0.1007 ($R^2$=0.9995). In all equations in this manuscript, x and y indicate the concentration of sulfide and the corresponding concentration-dependent signal, respectively. The limit of detection of the ITONP(drop-drying)/APTMS/ITO-based sensor for sulfide—at three standard deviations of the obtained signal in the absence of sulfide was calculated to be 3.0 μM.

EXAMPLE 9

Chronocoulometric Determination of Sulfide Concentration.

Figure 6A:
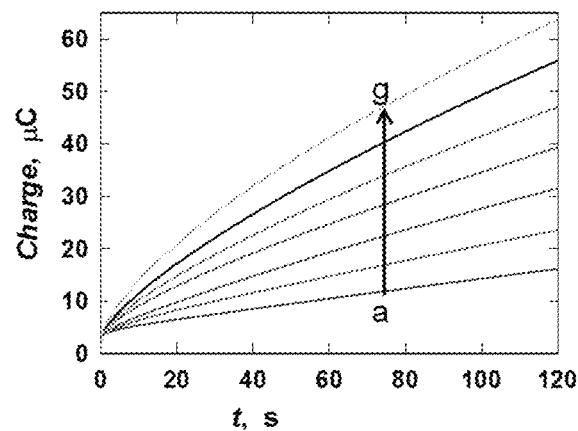
FIG. 6A shows chronocoulograms of an ITONP-modified ITO electrode (produced by drop-drying), in 25 mM Tris buffer and 50 mM $KNO_3$ at pH 8 and 0.3 V at concentrations of $Na_2S$ ranging from 0 μM (a) to 30 μM (g).
Figure 6B:
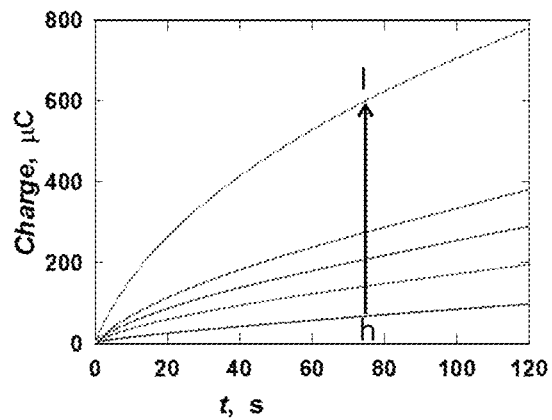
FIG. 6B shows chronocoulograms of an ITONP-modified ITO electrode (produced by drop-drying), in 25 mM Tris buffer and 50 mM $KNO_3$ at pH 8 and 0.3 V at concentrations of $Na_2S$ ranging from 50 μM (h) to 400 μM (l).
Figure 6C:
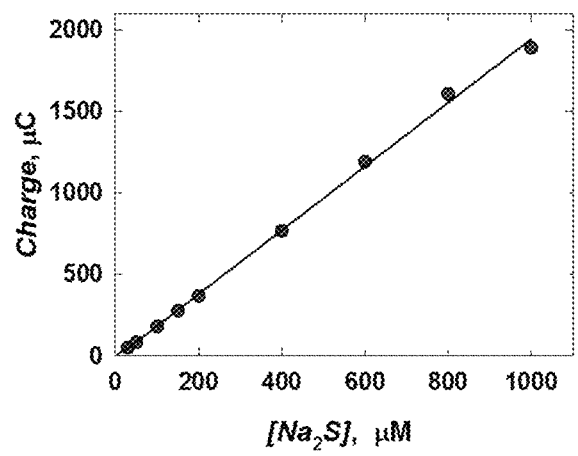
FIG. 6C shows the corresponding calibration plot of the chronocoulograms of FIGS. 6A and 6B for the concentration range of 30-1000 μM.
Figure 6D:
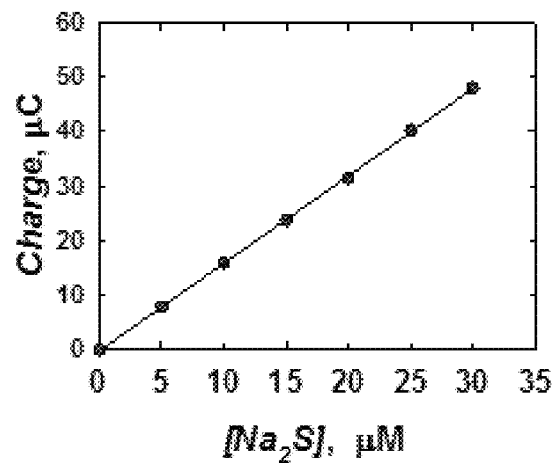
FIG. 6D shows the corresponding calibration plot of the chronocoulograms of FIGS. 6A and 6B for the concentration range of 5-30 μM.

To assess the performance of the amperometric method for determining the concentration of sulfide, chronocoulometric experiments for various concentrations of sulfide in 25 mM Tris buffer containing 50 mM $KNO_3$ (pH 8) at a 0.3 V applied potential using ITONP(drop-drying)/APTMS/ ITO were also carried out. FIGS. 6A and 6B show chronocoulograms recorded for the various sulfide concentrations. The charge generated due to oxidation of sulfide was observed to increase as the concentration of sulfide ion was increased. The corresponding calibration curve (FIG. 6C), plotted after subtraction of the mean of the zero sulfide response from the corresponding concentration-dependent signal, showed two linear regions: one between 5 μM and 30 and the other between 30 μM and 1000 μM. The obtained linear regression equations were y=1.1602x−0.1557 ($R^2$=0.9997) and y=1.9548x−12.2738 ($R^2$=0.998) for the low-concentration (5-30 μM) and high-concentration (30-1000 μM) regions of the curve, respectively. The detection limit was calculated using the linear regression obtained from the low-concentration region and was found to be 0.9 µM. This detection limit with ITONP(drop-drying)/APTMS/ITO is lower than that obtained in a previous study using a bare ITO electrode [M. A. Aziz, et al. *Electroanalysis*, 2015, 27, 1268-1275—incorporated herein by reference in its entirety].

EXAMPLE 10

Selectivity and Stability.

Various anions (sulfite, sulfate, chloride, carbonate, acetate, citrate, oxalate), elemental sulfur, benzene, toluene, and xylene, which are commonly present in the aqueous environment, may potentially interfere with the sulfide signal. Therefore, the chronocoulometric signal of a 100 µM sulfide solution was investigated in the presence of the mentioned interferents (FIG. 7). The chronocoulometric signal of 100 µM sulfide in the absence of any interferent and those signals in the presence of various interferents (each 100 µM) were observed to be similar. This study revealed the ITONP/APTMS(drop-drying)/ITO electrode to be highly selective for sensing sulfide. The stability of this electrode was also tested by acquiring six chronocoulograms of same electrode for 100 µM sulfide (data not shown). Almost identical sulfide oxidation signal in the first and sixth chronocoulograms were obtained. This result indicates the high stability of the developed ITONP(drop-drying)/APTMS/ITO electrode.

A preparation of an ITONP-modified ITO electrode for selective, sensitive, and stable amperometric and chronocoulometric detection of sulfides has been described. Drop-dying of an ITONP solution on a 3-aminopropyltrimethoxysilane-functionalized ITO (APTMS/ITO) electrode was found to be the most straightforward and effective preparation method of the various methods tested, and is also highly reproducible. ITONPs and ITONP-modified ITO were characterized by transmission electron microscopy (TEM) and field emission scanning electron microscopy (FE-SEM) images as well as optical photographs. The ITONP-modified ITO electrodes showed improved electrocatalytic properties toward sulfide electro-oxidation than did the bare ITO electrode. To further enhance sulfide electro-oxidation, various inert electrolyte and pH conditions were tested. The responses of the resulting ITONP-modified ITO electrode sensor to various sulfide concentrations were determined by carrying out amperometry (i-t) and chronocoulometry (CC) experiments. The detection limits obtained using amperometry and CC were 3.0 and 0.90 µM, respectively. Moreover, this ITONP-modified ITO electrode was highly selective toward sulfide in the presence of interfering species.

The invention claimed is:

1. An ITONP-modified ITO electrode, comprising:
a silanized ITO (indium tin oxide) electrode; and
ITO nanoparticles on the surface of the silanized ITO electrode, wherein the ITO nanoparticles have diameters of 10-210 nm.

2. The ITONP-modified ITO electrode of claim 1, wherein the ITO nanoparticles are in the form of semispherical nanoparticles having diameters of 10-20 nm and/or cubic nanoparticles having widths of 40-120 nm.

3. The ITONP-modified ITO electrode of claim 1, wherein the silanized ITO electrode is made from an ITO electrode having a sheet resistance of 15-45 Ω/sq.

4. The ITONP-modified ITO electrode of claim 1, wherein the ITO nanoparticles are distributed homogenously on the surface of the silanized ITO electrode.

5. A method for producing the ITONP-modified ITO electrode of claim 1, comprising:
reacting an ITO electrode with a solution comprising an alkoxysilane and an alcohol to produce the silanized ITO electrode;
contacting the silanized ITO electrode with an aqueous solution of ITO nanoparticles; and drying to produce the ITONP-modified ITO electrode.

6. The method of claim 5, wherein the solution comprises 0.5-4 vol % of the alkoxysilane relative to a total volume of the solution.

7. The method of claim 5, wherein the alkoxysilane is (3-aminopropyl) trimethoxysilane (APTMS).

8. The method of claim 5, which does not comprise annealing.

9. The method of claim 5, wherein 150-650 µg of ITO nanoparticles are in the aqueous solution for every 1 cm$^2$ of silanized ITO electrode contacted.

10. The method of claim 5, wherein the silanized ITO electrode is contacted by dropping the aqueous solution onto the silanized ITO electrode.

11. An electrolytic cell, comprising:
a working electrode comprising the ITONP-modified ITO electrode of claim 1 in contact with an electrolyte solution and
a counter electrode comprising platinum in contact with the electrolyte solution, wherein the electrolyte solution comprises 0.1 µM-10 mM aqueous sulfide.

12. The electrolytic cell of claim 11, having an aqueous sulfide limit of detection of 1-5 µM for an amperometric measurement.

13. The electrolytic cell of claim 11, having an aqueous sulfide limit of detection of 0.5-1.4 µM for a chronocoulometric measurement.

14. The electrolytic cell of claim 11, wherein a chronocoulometric measurement is substantially similar to a second chronocoulometric measurement of an otherwise identical second electrolytic cell further comprising at least one interferent in a second electrolyte solution,
wherein the interferent is at least one selected from the group consisting of sulfite, sulfate, chloride, carbonate, acetate, citrate, oxalate, elemental sulfur, benzene, toluene, and xylene.

15. The electrolytic cell of claim 11, further comprising a Ag/AgCl reference electrode in contact with the electrolyte solution.

16. The electrolytic cell of claim 11, wherein the electrolyte solution further comprises an inorganic salt at a concentration of 10 mM-1 M.

17. The electrolytic cell of claim 11, wherein the aqueous sulfide originates from hydrogen sulfide gas.

18. The electrolytic cell of claim 17, wherein the hydrogen sulfide gas is produced by at least one selected from the group consisting of petroleum extraction, petroleum refinement, natural gas extraction, natural gas refinement, fuel combustion, waste water treatment, tanneries, paper mills, and textile manufacturing.

19. The electrolytic cell of claim 11, which has a reproducible chronocoulometric measurement for five or more electrolyte solutions having substantially similar aqueous sulfide concentrations.

20. The electrolytic cell of claim 19, wherein the five or more electrolyte solutions have an aqueous sulfide concentration of 10-500 µM.

* * * * *